United States Patent
Moularat et al.

(10) Patent No.: US 9,260,738 B2
(45) Date of Patent: *Feb. 16, 2016

(54) PRODUCTION OF AN ASPERGILLUS CONTAMINATION IMPRINT BASED ON DETECTION OF MVOC

(71) Applicant: CENTRE SCIENTIFIQUE ET TECHNIQUE DU BATIMENT, Champs sur Marne (FR)

(72) Inventors: Stephane Moularat, Lognes (FR); Enric Robine, Lagny-sur-Marne (FR)

(73) Assignee: CENTRE SCIENTIFIQUE ET TECHNIQUE DU BATIMENT, Champs sur Marne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/024,904

(22) Filed: Sep. 12, 2013

(65) Prior Publication Data

US 2014/0080173 A1 Mar. 20, 2014

(30) Foreign Application Priority Data

Sep. 14, 2012 (FR) ...................................... 12 58646

(51) Int. Cl.
*C12Q 1/04* (2006.01)
*G01N 33/00* (2006.01)

(52) U.S. Cl.
CPC .............. *C12Q 1/04* (2013.01); *G01N 33/0047* (2013.01); *G01N 2333/38* (2013.01)

(58) Field of Classification Search
IPC ........................................................ C12Q 1/04
See application file for complete search history.

(56) References Cited

U.S. PATENT DOCUMENTS

| | | | |
|---|---|---|---|
| 2010/0107740 A1* | 5/2010 | Moularat ..................... | 73/31.03 |
| 2013/0244272 A1 | 9/2013 | Moularat et al. | |

OTHER PUBLICATIONS

Moularat et al. Detection of Fungal Development in Closed Spaces Through the Determination of Specific Chemical Targets; Chemosphere, vol. 72 (2008) pp. 224-232.*

Gao, Pegfie et al: Determination of Unique Microbial Volatile Organic Compounds Produced by Five Aspergillus Species Commonly Found in Problem Buildings, AIHA Journal, American Industrial Hygiene Association, Fairfax, VA, US, vol. 63, No. 2, Mar. 1, 2002, pp. 135-140.

Joblin Yael et al: Detection of Moulds by Volatile Organic Compounds; Application to Heritage Conservation; International Biodeterioration and Biodegradation, Eslevier Ltd., GB, vol. 64, No. 3, Jun. 1, 2010, pp. 210-217.

French Industrial Property Office, Search Report for priority application No. 1258646, Feb. 14, 2013.

Joblin, Yael, "Elaborboration of a Rapid and Continuous Air Analysing Microsystem for Fungal Canotaminatin Detection in Closed Spaces", pp. 30-73; May 12, 2011, Universite Paris Est, translation only.

French Industrial Property Office, Written Opinion for priority application No. 1258646, Sep. 14, 2012.

Chan et al. Determination of Organic Contaminants in Residual Indorrs Air Using an Adsorption-Thermal Desoprtion Technique; The Journal of the Air and Waste Management Association, vol. 40 (1990) pp. 62-67.

Moulerat at al. Detection of Fungal Development in Closed Spaces Through the Determination of Specific Chemical Targets; Chemosphere, vol. 72 (2008) pp. 224-232.

Zeringue et al. C15H24 Volatile Compounds Unique TP Aflatoxigenic Strains of Aspergillis Flavus; Applied and Environmental Microbiology, vol. 59, No. 7 (1993) pp. 2264-2270.

* cited by examiner

*Primary Examiner* — Kagnew H Gebreyesus
*Assistant Examiner* — Paul Martin
(74) *Attorney, Agent, or Firm* — Gottlieb, Rackman & Reisman, P.C.

(57) ABSTRACT

This invention proposes a method comprising the steps of:
(a) taking an air sample in an indoor environment, then
(b) detecting Microbial Volatile Organic Compounds (MVOCs) in the sample.

The step (b) comprises searching for a chemical imprint comprising at least one target molecule that is an MVOC associated with an *aspergillus* metabolism. Thanks to the invention, detection of such target molecules is easier and faster than detection of *aspergillus* strains or soluble *aspergillus* metabolites.

6 Claims, No Drawings

PRODUCTION OF AN ASPERGILLUS CONTAMINATION IMPRINT BASED ON DETECTION OF MVOC

TECHNICAL FIELD OF THE INVENTION

This invention relates to a method of determining a specific chemical imprint of an *aspergillus* contamination in indoor environments.

An indoor environment means a confined space inside a building that is not continuously ventilated. Examples of indoor environments are homes, museums, churches, cellars, historic monuments, administration buildings, schools and hospitals.

Fungal development is accompanied by the emission of MVOCs (Microbial Volatile Organic Compounds) at the beginning of their development and during all micromycete growth phases.

STATE OF PRIOR ART in this field, application WO 2004/051226 discloses methods of monitoring environments at risk for the presence or absence of microbes. This invention is characterized by the search for a cnp60 marker.

However, this document is restricted to the search for a chaperonin (cnp60) which requires cellular extractions that have to be selective of this chaperonin.

This type of method requires a significant growth of micromycetes, then the collection and extraction of chaperonin. Obviously, it is preferable to avoid the generation of micromycetes that are potentially dangerous for a human being. Furthermore, detection of chaperonin is found to be much more difficult than detection of VOC.

To overcome these disadvantages, the applicant developed a method of detecting a fungal contamination in an indoor environment by calculating a chemical fungal contamination index. This method is described in application WO 2008/125770. This tool was used to determine that micromycetes are present in 37 to 42% of French homes during the national Indoor Air Quality Observatory campaign (Moularat et al., 2008a).

However, this method cannot specifically conclude whether or not there is a risk of *aspergillus* contamination.

PRESENTATION OF THE INVENTION

In this context, the fungal contamination index developed by the application and disclosed in application WO 2008/125770 could be completed and refined for early detection of an *aspergillus* development.

To overcome the disadvantages of prior art, the applicant proposes a method of determining an *aspergillus* contamination risk in an indoor environment comprising steps to:
(a) take an air sample in an indoor environment, then
(b) detect MVOC in the sample.

The term "risk of *aspergillus* contamination" means the development of micromycetes of the *aspergillus* genus on a given support.

According to a first aspect, step (b) comprises searching for a chemical imprint comprising at least one target molecule that is a MVOC, associated with an *aspergillus* metabolism.

Particularly advantageously, detection of such target molecules is easier and faster than detection of *aspergillus* strains or soluble *aspergillus* metabolites.

According to a second embodiment, the applicant proposes a method of determining a risk of *aspergillus* contamination in an indoor environment comprising steps to:
(a) take an air sample in the indoor environment, then
(b) detect VOCs in the sample, which comprises detecting whether or not certain predetermined VOCs derived from fungal metabolism are present, these predetermined VOCs comprising at least one VOC from each of the following three VOC categories:
(1) VOCs that are emitted independently of the fungal species and its support and that are only emitted by fungal species;
(2) VOCs that are emitted independently of the fungal species and the support, and that are emitted by non-fungal biological species;
(3) VOCs that are emitted as a function of the fungal species and/or its support;
(c) calculate a chemical fungal contamination index depending on whether the predefined VOCs originating from fungal metabolism are or are not present.

According to a preferred variant, the method then comprises a step (d) to search for a chemical imprint comprising at least one target molecule that is a VOC associated with an *aspergillus* metabolism.

"Support" for a fungal species means the material on which the fungal species develops, preferably a construction material such as wallpaper, glass fabric or other.

Advantageously, the chemical imprint is specific to at least one *aspergillus* species chosen from among *Aspergillus restrictus, Aspergillus versicolor, Aspergillus sydowii, Aspergillus niger.*

Preferably, said target molecule is selected from among the group comprising 1,4-pentadiene, 4-heptanone, Dimethyldisulfide, Methoxybenzene, 1,3-butanediol, 1,4-hexadiene, 1-methoxy-2-methyl-benzene, 1-octen-3-one, 1-pentene, 2(5H)-furanone, 2-methyl-isoborneol, 3,3-dichloro-1-propene, 3-butyn-1-ol, 3-heptanol, 3-heptanone, 3-methyl-2-butanol, 3-methylhexane, 4-heptanol, 4-methyl-2-hexanone, Caryophyllene, Dimethyltrisulfide, Eremophilene, Germacrene D, Isoledene, Longifolene, Methyl-2-ethylhexanoate, Muurolane, Terpinolene.

As a variant, said target molecule is selected from the group comprising 1,4-pentadiene, 4-heptanone, Dimethyldisulfide, Methoxybenzene. These target molecules are specific to a plurality of *Aspergillus* strains.

According to another variant, said target molecule is selected from among the group comprising 1,3-butanediol, 1,4-hexadiene, 1-methoxy-2-methyl-benzene, 1-octen-3-one, 1-pentene, 2(5H)-furanone, 2-methyl-isoborneol, 3,3-dichloro-1-propene, 3-butyn-1-ol, 3-heptanol, 3-heptanone, 3-methyl-2-butanol, 3-methylhexane, 4-heptanol, 4-methyl-2-hexanone, Caryophyllene, Dimethyltrisulfide, Eremophilene, Germacrene D. Isoledene, Longifolene, Methyl-2-ethylhexanoate, Muurolane, Terpinolene. These target molecules are specific to one or two *Aspergillus* strains.

Thus, the method according to the invention can be made with one of said target molecules that is specific to one or two *aspergillus* strains. As a variant, this target molecule is specific to more than two *Aspergillus* strains.

According to one preferred variant, the chemical imprint comprises at least two target molecules, According to another variant, the chemical imprint comprises all said target molecules.

Advantageously, the method comprises a step to search for fungal contamination zones made before step (a). Thus, the method according to this variant begins with this step.

The method according to the second embodiment of the invention is particularly useful for early detection of a risk of *aspergillus* contamination, in other words before the appearance of significant quantities for a microbiological detection. This possibility of early detection is particularly attractive because it does not require direct detection of *aspergillus* species. It can thus be concluded that *aspergillus* contamination is present at an early stage of the development of fungi. "Early stage" of development means a stage at which micromycetes are invisible on the surface of the support and preferably undetectable by a microbiological analysis of air, but nevertheless produce metabolites and inhalable degradation products responsible for diseases in some cases.

DETAILED PRESENTATION OF ONE EMBODIMENT

This invention is based on a laboratory study of VOC emissions of 4 species of the *Aspergillus* genus:

*Aspergillus restrictus,*

*A. versicolor,*

*A. sydowii,*

*A. niger.*

These species have been cultivated protected from light and at 25° C. on different sterilized materials frequently found contaminated in indoor environments. A non-emissive reference support composed of glass fiber soaked in a nutrient solution, was also used for all tested strains. The nutrient solution used may for example be an aqueous solution comprising particularly K2HPO4, Kl, MgSO4, FeSO4, Glucose and NaNO3. This solution is buffered at a pH of 7.4.

Obviously, another known nutrient solution can be used without going outside the scope of the invention.

The handling plan is summarized in Table 1 below.

TABLE 1

Fungal strains tested as a function of the growth support

| | Reference support | Glass fabric | Cork | Ceiling tile | "Vinyl" wallpaper | Plaster board | Gelatin glued paper | Lignin free paper | Paper with lignin | Permanent paper | Linen |
|---|---|---|---|---|---|---|---|---|---|---|---|
| A. restrictus | X | | | | | | X | X | X | X | |
| A. versicolor | X | X | X | X | X | X | X | X | X | X | |
| A. sydowii | X | | | | | | | | | | X |
| A. niger | X | X | X | X | X | X | | | | | |

In table 1, an "X" indicates that the *aspergillus* strain (in rows) developed on the growth support (in columns) is identified.

In this case the reference support is a positive indicator to validate the capability of *aspergillus* strains to develop. The support used in this case is glass fiber soaked in a nutrient solution described above. Obviously, another known reference support could be used.

All the studied strains develop on the reference support and on at least one other growth support among those tested. The *A. sydowii* strain only grows on linen. The other strains *A. restrictus, A. versicolor, A. syclowii* and *A. niger* grow on more than two growth supports among those tested.

VOCs were identified during this study, solely from *Aspergillus* strains (Table 2):

TABLE 2

Compounds emitted in the presence of an *Aspergillus* development

| VOC | CASE No. | Aspergillus restrictus | Aspergillus versicolor | Aspergillus sydowii | Aspergillus niger |
|---|---|---|---|---|---|
| 1,4-pentadiene | 591-93-5 | X | X | X | X |
| 4-heptanone | 123-19-3 | X | X | X | X |
| Dimethyldisulfide | 624-92-0 | X | X | X | X |
| Methoxybenzene | 100-66-3 | X | X | X | X |
| 1,3-butanediol | 107-88-0 | | X | | |
| 1,4-hexadiene | 592-45-0 | X | | | |
| 1-methoxy-2-methyl-benzene | 578-58-5 | | X | | |
| 1-octen-3-one | 4312-99-6 | | | X | X |
| 1-pentene | 109-67-1 | X | X | | |
| 2(5H)-furanone | 497-23-4 | | X | | |
| 2-methyl-isoborneol | 2371-42-8 | | | | X |
| 3,3-dichloro-1-propene | 563-57-5 | X | | | |
| 3-butyn-1-ol | 927-74-2 | | | X | |
| 3-heptanol | 589-82-2 | | | | X |
| 3-heptanone | 106-35-4 | X | X | | |
| 3-methyl-2-butanol | 598-75-4 | | X | | |
| 3-methylhexane | 589-34-4 | | X | | |
| 4-heptanol | 589-55-9 | X | | | |

TABLE 2-continued

Compounds emitted in the presence of an *Aspergillus* development

| VOC | CASE No. | Aspergillus restrictus | Aspergillus versicolor | Aspergillus sydowii | Aspergillus niger |
|---|---|---|---|---|---|
| 4-methyl-2-hexanone | 105-42-0 | | | X | X |
| Caryophyllene | 87-44-5 | | | | X |
| Dimethyltrisulfide | 3658-80-8 | X | | | |
| Eremophilene | 10219-75-7 | | | | X |
| Germacrene D | 23986-74-5 | | | | X |
| Isoledene | 156108 | | | | X |
| Longifolene | 475-20-7 | | | | X |
| Methyl-2-ethylhexanoate | 816-19-3 | | X | | X |
| Muurolane | 29788-41-8 | | | | X |
| Terpinolene | 586-62-9 | | | | X |

Table 2 lists VOCs emitted in the presence of the different *Aspergilius* strains. Sampling and the analysis of these VOCs was done after 7 days incubation of strains at 25° C. Each "X" indicates identification of the VOC from growth of the species on at least one growth support.

As it can be seen in table 2, the first four VOCs are markers of four *aspergillus* species, while the other VOCs are markers of one or two *aspergillus* species.

Thus, this list of compounds may be split into 2 groups:

Compounds emitted by all tested *aspergillus* species (group 1 highlighted in gray in the table).

Compounds emitted by at least one and not more than three of the four tested *aspergillus* species (group 2).

From a practical point of view, after determining the presence of a fungal development, for example by the fungal contamination index, the search for specific targets listed in Table 2 can provide an alert on a probable development of *aspergillus* species. Indeed, the presence of at least one of these targets indicates the probable presence of a development of *aspergillus* species.

The number of identified tracers is correlated to the probability of the presence of an *Aspergillus* development. The fact that there are no compounds in group 1 reduces this probability.

Other target molecules may be identified. In general, target molecules of this type may consist of any VOC related to *aspergillus* metabolic schemes, in other words a VOC produced by an *Aspergillus* strain during the *aspergillus* metabolism.

Thus, the determination of an *aspergillus* contamination imprint based on the detection of specific chemical MVOCs can complete fungal contamination indexes already developed in application WO 2008/125770, by providing clear and reliable criteria for decisions for example concerning occupancy and renovation of contaminated buildings.

In one preferred variant of the method according to the invention, the following steps are carried out in sequence:
  a) take an air sample in an indoor environment, for example close to zones that are suspected of being contaminated;
  b) detect VOCs in the sample, which comprises detection of the presence or absence of certain predetermined VOCs originating from the fungal metabolism, these predetermined VOCs comprising at least one VOC from each of the following three VOC categories:
    (1) VOCs that are emitted independently of the fungal species and its support and that are only emitted by fungal species;
    (2) VOCs that are emitted independently of the fungal species and the support, but that may also have other biological origins; VOC with "other biological origins" refers particularly to VOCs emitted by non-fungal biological species;
    (3) VOCs that are emitted as a function of the fungal species and/or its support;
  c) calculate a chemical fungal contamination index as a function of whether or not predefined VOCs derived from fungal metabolism are present, in accordance with the method described in application WO 2008/125770, to determine if there is a fungal contamination;

The following steps are then also carried out to determine whether or not there is any *aspergillus* contamination:
  d) search for at least one target molecule that is a VOC derived from an *aspergillus* metabolism, particularly at least one target molecule selected from the group comprising 1,4-pentadiene, 4-heptanone, Dimethyldisulfide, Methoxybenzene, 1,3-butanediol, 1,4-hexadiene, 1-methoxy-2-methyl-benzene, 1-octen-3-one, 1-pentene, 2(5H)-furanone, 2-methyl-isoborneol, 3,3-dichloro-1-propene, 3-butyn-1-ol, 3-heptanol, 3-heptanone, 3-methyl-2-butanol, 3-methylhexane, 4-heptanol, 4-methyl-2-hexanone, Caryophyllene, Dimethyltrisulfide, Eremophilene, Germacrene D, Isoledene, Longifolene, Methyl-2-ethylhexanoate, Muurolane, Terpinolene; and preferably,
  e) search for a chemical imprint comprising at least two of said target molecules.

Interestingly, and in a new and inventive manner, the results derived from steps d) and e) can precisely, clearly and reliably determine whether or not there is any risk of *aspergillus* contamination.

This embodiment obviously gives more complete results than prior art, in that it is possible not only to conclude that a fungal contamination is present without any visible sign of fungal development, but also that an *aspergillus* development can be determined precisely and reliably.

In another variant of the invention, it is also possible to search for fungal contamination zones, then to take an air sample close to these fungal contamination zones before searching for said target molecule(s) mentioned above.

Such a search for fungal contamination zones may be done for example with the naked eye, by microscopy analyses or by microbiological or biochemical tests.

For example, air sampling may be done by diffusive sampling on a solid carbograph 4 type adsorbent. For example, detection may be done by gas phase chromatography followed by mass spectrometry (GC/MS). Other detection methods may be used.

Many combinations may be envisaged without going outside the scope of the invention; those skilled in the art can choose one or the other as a function of the implementation constraints that they have to respect.

The invention claimed is:

1. A method of determining a risk of *aspergillus* contamination in an indoor environment comprising steps of:
   (a) searching for fungal contamination zones in an indoor environment;
   (b) taking an air sample from said indoor environment where sampling is carried out by diffusive sampling over a solid absorbent of graphitized carbon black; then
   (c) detecting Microbial Volatile Organic Compounds (MVOCs) in the sample at least by gas chromatography followed by mass spectrometry (GC/MS), wherein step (c) comprises searching for a chemical imprint comprising at least five target molecules that are MVOC associated with an *aspergillus* metabolism by comparing the MVOC detected to a list of MVOCs associated with *aspergillus* contamination,
   wherein the chemical imprint is specific to at least one *aspergillus* species chosen from among *Aspergillus restrictus*, *Aspergillus versicolor*, *Aspergillus sydowii*, and *Aspergillus niger*,
   wherein said target molecules are specific to one or two *aspergillus* strains, wherein said target molecules are selected from among the group comprising 1,4-pentadiene, 4-heptanone, Dimethyldisulfide, Methoxybenzene, 1-octen-3-ol, 1-pentene, 3-heptanone, 4-methyl-2-hexanone and Methyl-2-ethylhexanoate.

2. The method according to claim 1, wherein the step (c) comprises the following substeps before searching for a chemical imprint comprising at least one target molecule that is an MVOC associated with an *aspergillus* metabolism:
   detecting whether or not certain predetermined VOCs derived from fungal metabolism are present, these predetermined VOCs comprising at least one VOC from each of the following three VOC categories:
   I. VOCs that are emitted independently of the fungal species and its support and that are only emitted by fungal species;
   II. VOCs that are emitted independently of the fungal species and the support, and that are emitted by non-fungal biological species;
   III. VOCs that are emitted as a function of the fungal species and/or its support; and
   calculating a chemical fungal contamination index as a function of whether or not predefined VOCs derived from fungal metabolism are present.

3. The method of claim 1, wherein the chemical imprint is specific to *Aspergillus restrictus* and comprises all of the target molecules 1,4-pentadiene, 4-heptanone, Dimethyldisulfide, Methoxybenzene, 1,4-hexadiene, 1-pentene, 3,3-dichloro-1-propene, 3-heptanone, 4-heptanol and dimethyltrisulfide.

4. The method of claim 2, wherein the chemical imprint is specific to *Aspergillus versicolor* and comprises all of the target molecules 1,4-pentadiene, 4-heptanone, Dimethyldisulfide, Methoxybenzene, 1,3-butanediol, 1-methoxy-2-methylbenzene, 1-pentene, 2(5H)-furanone, 3-heptanone, 3-methyl-2-butanol, 3-methylhexane and Methyl-2-ethylhexanoate.

5. The method of claim 1, wherein the chemical imprint is specific to *Aspergillus sydowii* and comprises all of the target molecules 1,4-pentadiene, 4-heptanone, Dimethyldisulfide, Methoxybenzene, 1-octen-3-ol, 3-butyn-1-ol and 4-methyl-2-hexanone.

6. The method of claim 1, wherein the chemical imprint is specific to *Aspergillus niger* and comprises all of the target molecules 1,4-pentadiene, 4-heptanone, Dimethyldisulfide, Methoxybenzene, 1-octen-3-ol, 2-methyl-isoborneol, 3-heptanol, 4-methyl-2-hexanone, Caryophyllene, Eremophilene, Germacrene D, Isoledene, Longifolene, Methyl-2-ethylhexanoate, Muurolane, and Terpinolene.

* * * * *